United States Patent
Veach et al.

(10) Patent No.: US 6,847,207 B1
(45) Date of Patent: Jan. 25, 2005

(54) ID-OD DISCRIMINATION SENSOR CONCEPT FOR A MAGNETIC FLUX LEAKAGE INSPECTION TOOL

(75) Inventors: William D. Veach, Salt Lake City, UT (US); Tyler S. Lloyd, Murray, UT (US); Jed C. Ludlow, North Salt Lake, UT (US)

(73) Assignee: TDW Delaware, Inc., Wilmington, DE (US)

( * ) Notice: Subject to any disclaimer, the term of this patent is extended or adjusted under 35 U.S.C. 154(b) by 0 days.

(21) Appl. No.: 10/825,873

(22) Filed: Apr. 15, 2004

(51) Int. Cl.[7] .............................................. G01R 33/12
(52) U.S. Cl. ...................................................... 324/220
(58) Field of Search ................................ 324/219–222, 324/238–240, 242–243; 73/592, 622, 623

(56) References Cited

U.S. PATENT DOCUMENTS

| | | | |
|---|---|---|---|
| 3,949,292 A | 4/1976 | Beaver et al. ................. | 324/37 |
| 4,769,598 A | 9/1988 | Krieg et al. ................. | 324/219 |
| 4,945,306 A | 7/1990 | Lowther ...................... | 324/220 |
| 4,964,059 A | 10/1990 | Sugaya et al. .............. | 364/507 |
| 5,283,520 A | 2/1994 | Martin et al. ................ | 324/220 |
| 5,293,117 A | 3/1994 | Hwang ........................ | 324/220 |
| 5,506,505 A | 4/1996 | Worthen et al. ............ | 324/326 |
| 5,565,633 A | 10/1996 | Wernicke .................... | 73/865.8 |
| 5,864,232 A | 1/1999 | Laursen ...................... | 324/220 |
| 6,023,986 A | 2/2000 | Smith et al. ................ | 73/866.5 |
| 6,640,655 B1 | 11/2003 | Manzak et al. ............ | 73/865.8 |
| 6,683,452 B2 | 1/2004 | Lee et al. .................... | 324/240 |

OTHER PUBLICATIONS

Full–Signature Multiple–Channel Vertilog by G.W. Adams and W.D. Moffat published in May 1991 in the *Society of Petroleum Engineers*.

*Primary Examiner*—Bot LeDynh
(74) *Attorney, Agent, or Firm*—Gable & Gotwals; Paul H. JOhnson

(57) ABSTRACT

An instrument pig and method of operation thereof for determining the characteristics of a ferromagnetic pipeline through which it passes, including a pig body, first and second coaxial circumferential, spaced apart magnets of opposed polarities supported to the pig body and providing substantially complete magnetic saturation of an area of the pipeline between the magnets, first instruments between the magnets and arranged to generate signals that are responsive to flux leakage servicing to provide first information as to anomalies in the pipeline interior and/or exterior surfaces, second instruments supported by the pig body between said magnets and arranged to generate signals that are responsive to eddy currents induced in the pipeline interior surface servicing to provide second information as to anomalies in the pipeline interior surface, signal processing circuitry combining the first and second signals and wherein the second instruments are energized only in response to signals generated by said signal processing circuitry.

16 Claims, 4 Drawing Sheets

ID-OD DISCRIMINATION SENSOR CONCEPT FOR A MAGNETIC FLUX LEAKAGE INSPECTION TOOL

REFERENCE TO PENDING APPLICATIONS

This application is not based upon any pending domestic or international patent applications.

REFERENCE TO MICROFICHE APPENDIX

This application is not referenced in any microfiche appendix.

FIELD OF THE INVENTION

Disclosed herein is a pipeline inspection instrument pig having ID-OD discrimination. The instrument pig functions by flux leakage detection coupled with an eddy current system providing means for discriminating between anomalies in the pipeline exterior and interior surfaces. ID-OD discrimination is accomplished employing an eddy current pulser coil and an eddy current detection coil to provide a signal used to indicate whether a detected flux leakage anomaly is in the pipeline interior surface.

BACKGROUND OF THE INVENTION

The Prior Art

The use of magnetic flux leakage inspection tools in pipelines is an established technology. Flaws in ferromagnetic pipes have been detected by establishing a magnetic field in the wall of the pipe and detecting flux leakage caused by anomalies in the pipe wall. Distortion of the magnetic field caused by anomalies such as corrosion, pits, or changes in the structure of the pipe wall, some of which can be caused by couplings, welds, collars, or so forth, can be found, measured, and identified in recorded information. Flux leakage pipeline inspection tools therefore provide an established method of determining the characteristics of a pipeline through which an inspection pig passes.

One problem which has existed with reference to flux leakage inspection tools is that of identifying whether a detected flux leakage is occasioned by anomalies, such as corrosion, on the interior or exterior pipe wall surface. When making an inspection of a pipeline it is important to record the location and size of anomalies in the pipe wall as well as of the anomaly identified as to whether it exists on the pipe interior surface or the pipe exterior surface.

A known means of measuring flux leakage is by the use of a Hall-effect device.

Flux leakage inspection instrument pigs typically include the use of a plurality of armatures, each having at one end a positive magnetic pole and at the other end a negative magnetic pole. The magnets are constructed and dimensioned so as to substantially magnetically saturate a short circumferential length of the pipe as the inspection pig moves through the pipe.

For background information relating to instrument pig used for pipeline inspection and particularly pigs that detect anomalies by measuring flux leakage, reference can be made to the following previously issued United States Patents:

| PATENT NUMBER | DATE OF ISSUE | TITLE |
|---|---|---|
| 3,949,292 | Apr. 6, 1976 | Pipeline Inspection Device with Pivotal Support Structure |
| 4,769,598 | Sep. 6, 1988 | Apparatus for Electromagnetically Testing the Walls of Pipelines |
| 4,945,306 | Jul. 31, 1990 | Coil and Hall Device Circuit for Sensing Magnetic Fields |
| 4,964,059 | Oct. 16, 1990 | Apparatus for Inspecting A Pipeline |
| 5,283,520 | Feb. 1, 1994 | Method of Determining Thickness of Magnetic Pipe by Measuring the Time It Takes the Pipe To Reach Magnetic Saturation |
| 5,293,117 | Mar. 8, 1994 | Magnetic Flaw Detector for Use with Ferromagnetic Small Diameter Tubular Goods Using A Second Magnetic Field To Confine A First Magnetic Field |
| 5,506,505 | Apr. 9, 1996 | Apparatus for Remotely Indicating Pipeline Pig Including A Sensor Housing Having Surface Engaging Orthogonally Disposed Paramagnetic Materials A Solid State Sensor and A Flag |
| 5,565,633 | Oct. 15, 1996 | Spiral Tractor Apparatus and Method |
| 5,864,232 | Jan. 26, 1999 | Magnetic Flux Pipe Inspection Apparatus for Analyzing Anomalies In A Pipeline Wall |
| 6,023,986 | Feb. 15, 2000 | Magnetic Flux Leakage Inspection Tool for Pipelines |
| 6,640,655 | Nov. 4, 2003 | Self Tracking Sensor Suspension Mechanism |
| 6,683,452 | Jan. 27, 2004 | Magnetic Flux Density Apparatus for, e.g., Detecting An Internal Crack of A Metal or A Shape of the Metal |

In addition to the above-listed patents, a relevant reference is an article published in the Society of Petroleum Engineers in May 1991 entitled "Full-Signature Multiple-Channel Vertilog," G. W. Adams and W. D. Moffat, authors.

BRIEF SUMMARY OF THE INVENTION

The instrument pig of this invention is used for determining the characteristics of a ferromagnetic pipeline through which it passes. The essential features of the instrument pig include a pig body that is coaxially supported within a pipeline and is configured with cups to cause the pig body to move within the pipeline in response to fluid flow. "Fluid" as used herein includes liquids, gases or combinations thereof.

Supported to the pig body are a plurality of first and second coaxial, circumferential spaced apart magnets of opposed polarities. The pairs of magnets are arranged circumferentially around the pig body with the magnetic poles spaced close to the pipeline interior circumferential wall. The spaced apart magnets of opposed polarities are configured for providing substantially complete magnetic saturation of a circumferential area of the pipeline between the magnets, the fully magnetized area of the pipeline constantly moving with the pipeline pig body as it moves through the pipeline.

Affixed to the pig body are first instruments that are supported between the magnetic poles and arranged to generate signals that are responsive to flux leakage. Flux leak from the fully magnetized section of the pipeline occurs as a consequence of anomalies appearing in the interior or exterior circumferential surfaces of the pipeline wall.

A second instrument is supported by the pig body between the poles of the magnets and arranged to generate signals that are responsive to eddy currents induced in the pipeline interior surface. By measuring induced eddy currents, indication can be obtained of whether a detected anomaly exists in the interior surface. If an anomaly is detected that occurs as a consequence of flux leakage and if the eddy current instruments indicate that the pipeline interior circumferential wall is free of anomalies, then by logic it is concluded that the detected anomaly is in the pipeline exterior surface. If an anomaly is detected and simultaneously the eddy current instrumentation indicates the existence of an anomaly in the interior pipeline surface, then the logic system provides an indication that the detected anomaly is on the pipeline interior surface.

Determining whether a detected anomaly is on the interior or exterior surface is thereby obtained by combining the first and second signals to indicate both the magnitude and the interior or exterior location of the pipeline anomalies.

Energy is required to induce eddy currents into the interior surface of a pipeline, and typical eddy current sensing systems can consume substantial amounts of energy for continuous operation. It is necessary to introduce and then measure eddy currents only when measurements need to be recorded. For this reason, in the instrument pig herein, the eddy current instruments are energized only when requested by a signal processing circuit.

While flux leakage can be detected in various ways, a very successful and a preferred system for practicing the invention herein includes the use of Hall-effect devices.

The invention herein can be further summarized as a method of determining the characteristics of the interior and exterior surfaces of a metal pipeline, including the steps of (a) moving an axially supported pig body through a pipeline; (b) by means carried by the pig body, magnetically saturating a circumferential zone of the pipeline that moves with the instrument pig; (c) continuously measuring changes of reluctance in the moving circumferential magnetized zone of the pipeline to provide indications of the presence and size of anomalies in the pipeline interior or exterior surfaces; (d) electrically actuating a plurality of pulse coils to induce eddy currents in the internal surface of the moving circumferential zone of the pipeline; (e) by means of a plurality of sensing coils, each paired with a pulse coil, measuring the eddy currents to determine the presence or absence of an anomaly in the pipeline interior surface; (f) comparing the results of steps in (c) and (e) to determine whether an anomaly detected in step (c) is on the interior or exterior of the surface of the pipeline; (g) recording the results of steps (c) and (f) to provide information as to the anomaly's size and interior/exterior location with respect to the pipeline wall; and (h) energizing said plurality of pulse coils in step (d) only generated by said signal processing circuitry.

A better and more complete understanding of the invention will be obtained from the following detailed description of the preferred embodiments, and the claims, taken in conjunction with the attached drawings.

DETAILED DESCRIPTION OF THE PREFERRED EMBODIMENTS

It is to be understood that this invention is not limited to the details of construction and arrangement of components illustrated in the accompanying drawings. The invention is capable of other embodiments and of being practiced or carried out in a variety of ways. Further, the phraseology and terminology employed herein are for purposes of description and not of limitation.

Elements employed in illustrating the practice of the instrument pig and the methods of determining the characteristics of the interior and exterior surfaces of a metal pipeline, as illustrated in the attached drawings, will be identified by numbers indicated hereinbelow:

| | |
|---|---|
| 10 | instrument pig |
| 12 | instrumentation section |
| 14 | elastomeric cups |
| 16 | instrument support package |
| 18 | odometers |
| 20 | pig body |
| 22 | A&B end plates |
| 24 | armatures |
| 26 | positive pole magnet |
| 29 | negative pole magnet |
| 30 | forward link arm |
| 32 | rearward link arm |
| 34 | pin |
| 36 | slot |
| 38 | spacers |
| 40 | Hall-effect sensor |
| 42 | interior circumferential surface |
| 44 | pipeline |
| 46 | exterior circumferential surface |
| 48 | range of measurement |
| 50 | eddy current sensor system |
| 54 | induced eddy currents |
| 56 | head assembly |
| 58 | sensed eddy current |
| 60 | Hall-effect process circuitry |
| 62 | 62A-D |
| 64 | eddy current pulser circuit |
| 66 | eddy current process circuit |
| 68 | output signal |
| 70 | signal processing and output circuit |
| 72 | Hall-effect instrumentation |
| 74 | eddy current instrumentation |
| 76 | conductor |
| 78 | conductor |
| 80 | conductor |
| 82 | conductor |
| 84 | conductor |
| 86 | odometer wheel |
| 88 | odometer circuit |
| 90 | positioning signal |

-continued

| 92 | conductor |
| 94 | recorder |

Figure 1:
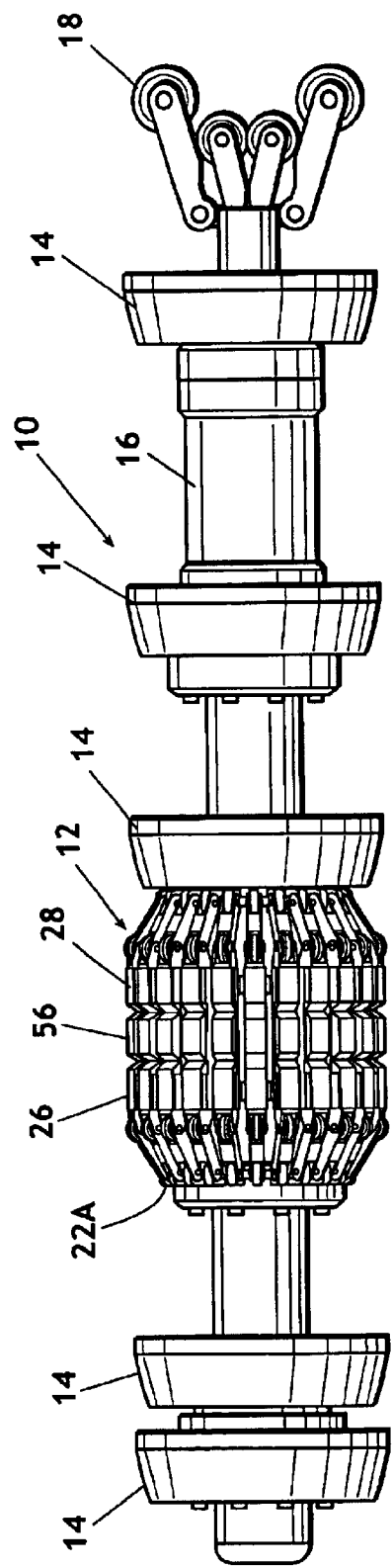
FIG. 1 is an elevational view of a pipeline pig assembly of a type that can be employed in practicing the invention. The pipeline pig in FIG. 1 includes cups for contacting the interior surface of a pipeline wall and for causing the pig to move by fluid flow, either liquid or gas, through the pipeline.

Referring to FIG. 1, a typical instrument pipeline pig of the type that can employ the principals of this invention is illustrated. The overall pipeline instrument pig is indicated generally by the numeral 10 and includes an instrumentation section 12 to which this invention is specifically directed. The typical instrument pipeline pig 10 includes the use of a plurality (5 being shown) of elastomeric cups 14 that have two basic functions. First, the cups 14 support the pipeline pig centrally within the pipeline, and second, they have circumferential edges or lips that engage a pipeline interior wall, forming a piston-like relationship so that fluid flowing through the pipeline causes a force against the cups that moves the instrument pipe 10 through the pipeline.

In addition to the instrumentation section 12, a typical pipeline pig 10 includes as illustrated, an instrument support package 16 that typically contains batteries by which electrical energy is supplied to the instrumentation section 12, and recording instruments. Instrument support package 16 is connected to the instrumentation section 12 by means of an internal cable (not shown).

Further, the typical pipeline pig includes an odometer 18 that is in the form of a wheel that engages the pipeline interior wall surface to provide electrical signals by which the location of detected anomalies in the pipeline wall are recorded.

It must be understood that the instrument pig 10 is illustrated by way of example only and not by limitation. The invention herein lies exclusively within the arrangement of the instrumentation section 12 and such instrument section can be used in conjunction with other instrument pig systems.

Figure 2:
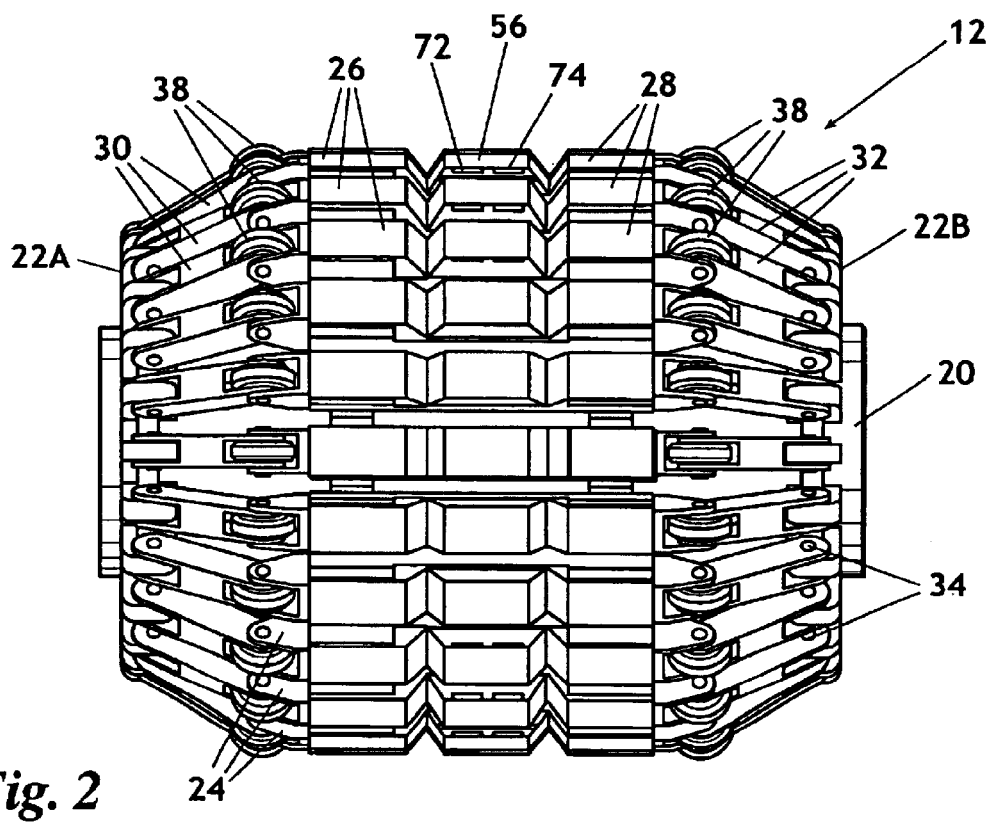
FIG. 2 is an elevational view of the instrument portion of the pipeline pig of FIG. 1 showing a plurality of paralleled, closely spaced apart armatures with permanent magnets. The armatures are attached by link arms to the pig body.
Figure 3:
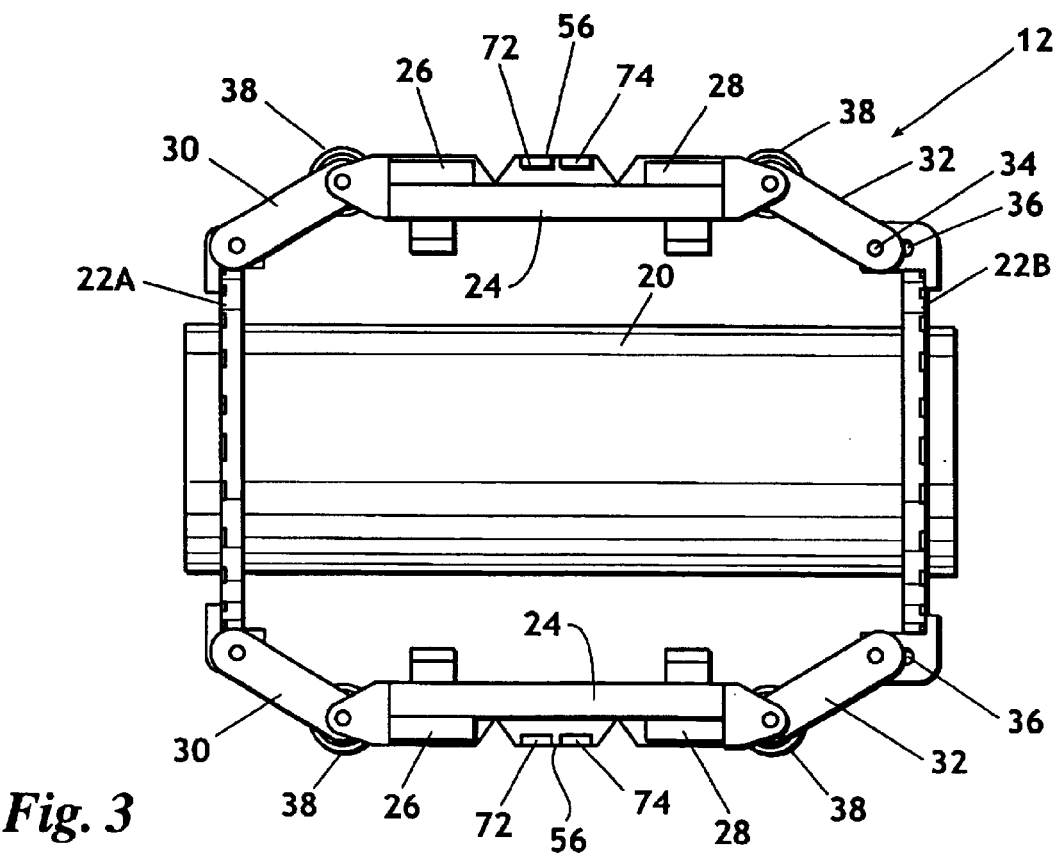
FIG. 3 is an elevational cross-sectional view of FIG. 2 showing only a top and bottom positioned armature with its magnets, spacers, linkages, and instruments employed in this invention.

The instrumentation section 12 is illustrated in greater detail in FIGS. 2–6. Referring to FIGS. 2 and 3, a basic structural arrangement of an instrumentation system by which this invention can be practiced is illustrated. The instrumentation section 12 includes a pig body 20 having spaced apart end plates 22A and 22B. Supported between the end plates are a plurality of elongated armatures 24 that are in closely spaced parallel arrangement and positioned circumferentially around the pig body 20. Each armature 24 supports at one end a positive pole magnet 26 and at the other end a negative pole magnet 28. Rather than being called "negative" and "positive" pole magnets, they are frequently referred to as north pole and south pole magnets. Magnets 26 and 28 mounted on associated armatures 24 are closely spaced and of magnetic intensity so that the circumferential portion of the length of the pipe between magnets 26 and 28 is at least substantially fully magnetically saturated.

Each armature 24 is supported between plates 22A and 22B by a forward link-arm 30 and a rearward link-arm 32. Each of the forward link-arms 30 is pivoted at one end to plate 22A and at the rearward end to an armature 24. The rearward link-arms 32 are each pivoted to an armature 24 at one end and the rearward end has a pin 34 received in a slot 36. The link arms 30 and 32 thereby allow flexible radial position of each armature 24 with respect to the pig body 20—that is, each armature can be deflected inwardly and outwardly as required to conform to the internal cylindrical surface of the pipe wall through which the instrument pig travels.

To maintain the magnets 26 and 28 in close proximity to the interior pipeline wall but at the same time prevent the magnets from being worn by engagement with the pipeline wall, spacers 38 are employed. Spacers 38 may be wheels as illustrated in the drawings or may be pads arranged to slide against the internal wall of the pipeline to thereby space the magnets 26 and 28 in close proximity to the pipeline wall but without touching the wall. The use of wheels functioning as spacers is a known technology and not a part of this invention.

Figure 5:
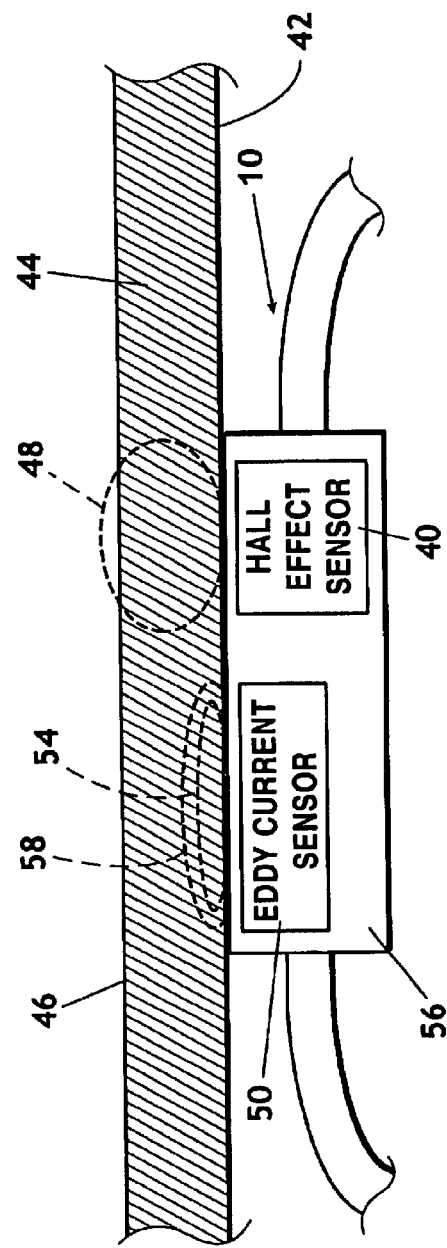
FIG. 5 is a diagrammatic elevational, cross-sectional view showing a portion of a pipeline wall and showing the basic instruments employed in the invention including a Hall-effect sensor assembly and in combination an eddy current sensor.
Figure 6:
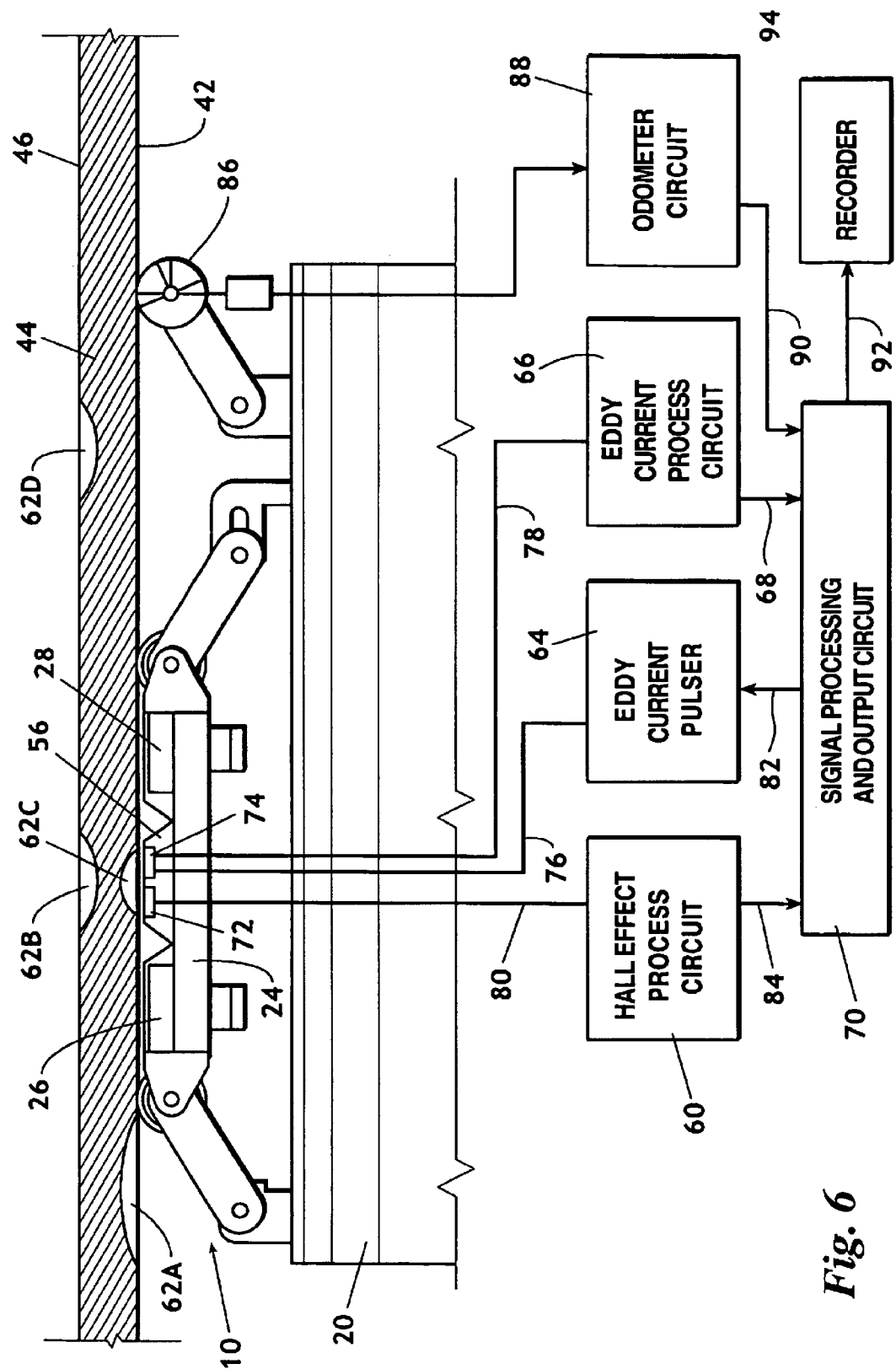
FIG. 6 is a diagrammatic elevational view of a portion of an instrument pig used to practice the invention. This view illustrates a pig body with one armature with its attached magnets and instrumentation positioned between the magnets. By block diagram, the basic electronics used to practice the invention are illustrated.

The essence of the invention is best illustrated by referring to FIGS. 5 and 6. FIG. 5 diagrammatically illustrates the basic concepts. The instrument pig 10 as generally indicated in FIG. 5 carries with it instrumentation that includes essentially a Hall-effect sensor 40 supported by the instrument in close proximity to the interior circumferential surface 42 of a cylindrical pipeline 44 that has a corresponding exterior circumferential surface 46. The use of Hall-effect sensors 40 is known technique for detecting flux leakage in a magnetically saturated pipe wall. The range of detection of anomalies obtained by Hall-effect sensor 40 is indicated by the dotted lines 48 in FIG. 5.

If the instrument pig 10 of this invention included instrumentation that contained only Hall-effect sensors, it would function to provide a record indicative of anomalies in the pipe wall but such record would not provide information as to whether the detected anomalies are on the pipe interior circumferential surface 42 or the exterior circumferential surface 46. To provide this lacking information, the instrument package of the instrument pig of this invention includes the use of eddy current sensor systems 50. An "eddy current" is, generally speaking, an induced electric current in an electrically conductive object that typically causes a loss of energy. Eddy currents are sometimes also called "Foucault currents." Eddy currents move contrary to the direction of a main current and usually in a circular motion. A unique characteristic of eddy currents is that when induced into a conductive object, they typically are confined to a shallow depth of the skin surface of the object. This characteristic is taken advantage of in the present invention in that, as illustrated in FIG. 5, each eddy current sensor system 50 functions by inducing an eddy current indicated by the dotted lines 54 into the interior circumferential surface 42 of pipeline wall 44. The eddy currents 54 are induced by pulsing a coil carried by the eddy currents sensor system 54.

Eddy current sensors are often employed to measure the proximity of electrically conductive materials. They exploit the "skin depth" effects that result from exposing a conductive material to a high-frequency magnetic field. As such, their effective field of view into the material is limited to a few thousandths of an inch. Additionally, they are able to operate inside a strong low-frequency magnetic field with little effect on performance.

Figure 4:
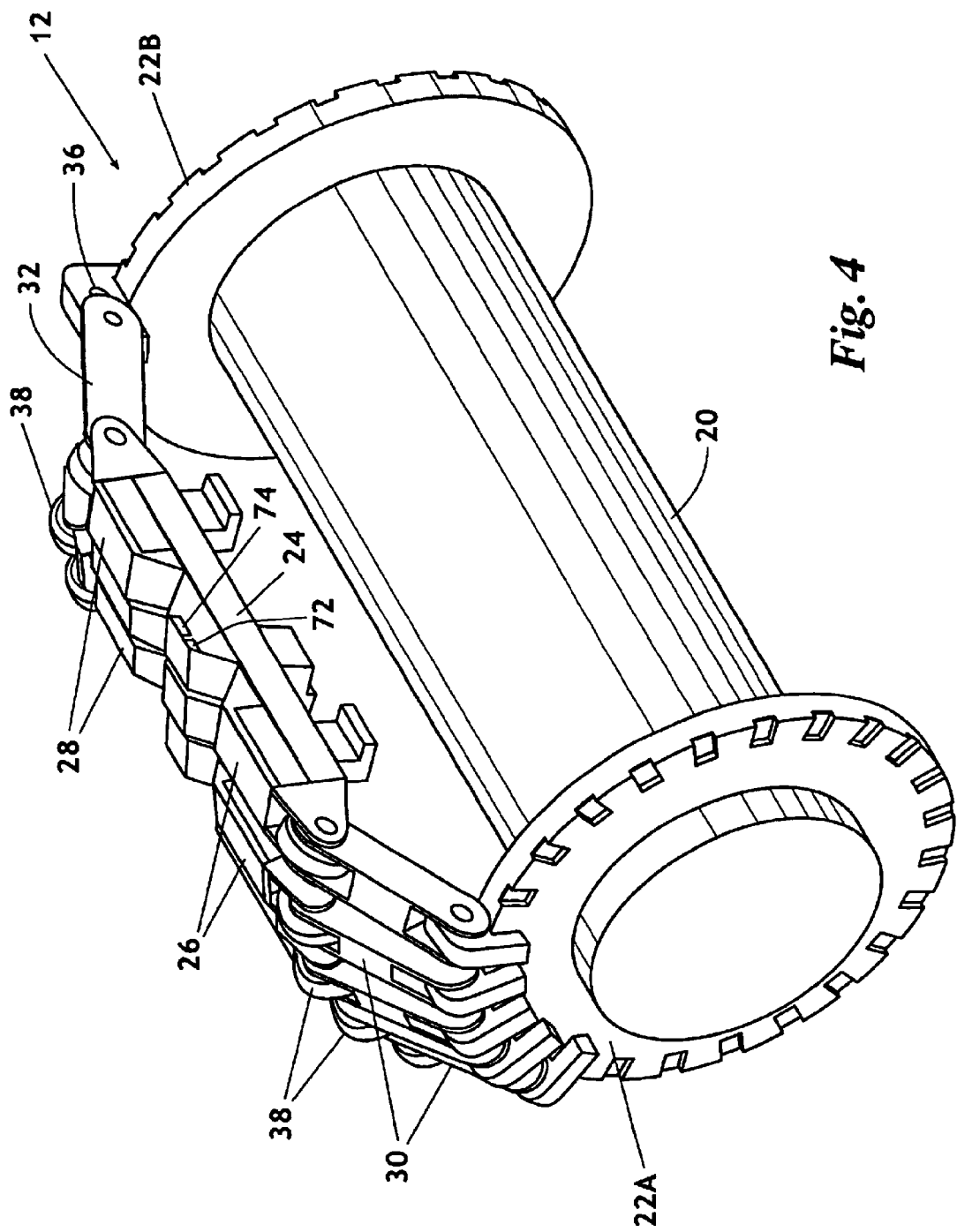
FIG. 4 is a partial isometric view showing a typical pipeline pig body and representative armatures with associated magnets, instruments, spacers, and linkages as employed in the invention.

The sensor concept disclosed in FIG. 5 incorporates both the Hall-effect sensor 40 and the eddy current sensor system 50 that are supported in the same head assembly, such head assemblies 56 being seen best in FIGS. 3, 4 and 6. The system of this invention employs Hall-effect sensors 40 as primary quantitative indicators of metal loss and therefore the existence of anomalies in the pipe wall interior and exterior circumferential surfaces 42 and 46. This is so since the field of view, that is the range of measurement 48 seen in FIG. 5, includes the entire pipe wall 44. However the eddy current sensors see only a short depth into the interior pipe wall 42 and responds to metal loss that is localized to the inside wall of the pipe.

The eddy current sensor systems 50 employ the use of a pulse coil design to minimize the power required. This is illustrated in FIG. 5 by an induced eddy current 54 and a sensed eddy current represented by the dotted lines of 58. The quantitative extent of sensed eddy currents indicate the presence or absence of anomalies, that is missing metal, from the interior circumferential surface 42 of pipe 44.

An important feature of the present invention is that the eddy current sensor system 50 is energized or excited to produce the induced eddy current 54 only as requested from the instrument electronics. This is schematically represented in FIG. 6 which shows Hall-effect process circuitry 60 that responds to detected anomalies 62A through 62D in the wall of pipeline 44. When requested by the signal processing circuit 70, eddy current pulser circuit 64 is activated to stimulate the eddy current sensor system 50 to initiate induced eddy current represented by 54 in FIG. 5. An eddy current process circuit 66 responds sensed eddy current 58 (FIG. 5) and provides an output signal on conductor 68 to signal processing output circuit 70.

FIG. 6 indicates schematically a portion of the instrument pig 10 of this invention showing the pig body 20, an armature 24, positive and negative magnets 26 and 28 as supported on the armature and a head assembly 56 positioned between the magnets that contain Hall-effect instrumentation 72 and eddy current instrumentation 74. Eddy current instrumentation 74 responds to eddy current pulser circuit 64 to cause induced eddy currents 54 as seen in FIG. 5 and for detecting and measuring resultant sensed eddy current flow indicated by the numeral 58 in FIG. 5. As shown in FIG. 6, the eddy current pulser signal is carried by conductor 76 to eddy current instrument 74 while the sensed eddy current is carried by conductor 78 to eddy current processing circuit 66. The conductor 80 carries the signal from Hall-effect instrumentation 72 to the Hall-effect processing circuitry 60. Initiating signals from processing circuit 70 to actuate eddy current pulser 64 are carried by conductor 82 while the quantitative process signal generated by the Hall-effect instrument 72 is passed by conductor 84 to signal processing and output circuit 70.

FIG. 6 shows the use of an odometer wheel 86 supplying signals to an odometer circuit 88 which provides a positioning signal 90 to signal processing and output circuit 70.

While ID/OD discrimination sensors have conventionally been arranged in a second array of heads located somewhere away from the magnetizer systems of an instrument pig, in the invention herein the Hall-effect sensor 72 and eddy current instrumentation 74 are in the same head assembly 56 positioned between magnetic poles 26 and 28. This system eliminates the need for a secondary sensor array located elsewhere on a tool and subsequently reduces the number of connectors and cables required to pass signals from the sensor heads to the data logging electronics.

In summary, first instrumentation Hall-effect instrumentation 72 that is included in head assembly 56 and positioned between magnetic pole 26 and 28 is arranged to generate signals by way of conductor 80 that are responsive to flux leakage and thereby serves to provide first information as to anomalies 62A through 62D in the pipeline interior or exterior surfaces 42 and 46. Second instrumentation, that is, eddy current instrumentation 74, is supported by head assembly 56 between magnets 26 and 28 and arranged to generate signals that are responsive to eddy currents 54 and 58 as seen in FIG. 5 that are induced in the pipeline interior surface 42 that provides second information as to anomalies in the interior wall 42 of the pipeline 44. An important feature of the invention herein as illustrated in the schematic circuit diagram of FIG. 6 is that the second eddy current instrumentation is energized only in response to signals generated by signal processing circuit 70. In this way the energy required to operate eddy current instrumentation 74 is employed only when data is required and thus substantial energy saving is obtained.

The invention described herein is not limited to the specific illustrations contained in the drawings which are representative only of one embodiment of the invention which are presented to be a preferred embodiment at the time of the preparation of this application, but it is understood that the invention is limited only by the scope of the attached claim or claims including the full range of equivalency to which each element or step thereof is entitled.

What is claimed is:

1. An instrument pig for determining the characteristics of a ferromagnetic pipeline through which it passes, comprising:

a pig body coaxially supported and moving within the pipeline in response to fluid flow;

first and second coaxial circumferential, spaced apart magnets of opposed polarities supported to said pig body and providing substantially complete magnetic saturation of an area of the pipeline between the magnets;

first instruments supported by the pig body between said magnets and arranged to generate signals that are responsive to flux leakage servicing to provide first information as to anomalies in the pipeline interior and/or exterior surface;

second instruments employing pulsed and sensing coil pairs supported by the pig body between said magnets and arranged to generate signals that are responsive to eddy currents induced in the pipeline interior surface servicing to provide second information as to anomalies in the pipeline interior surface;

signal processing circuitry combining said first and second signals to indicate the magnitude and interior or exterior location of the pipeline anomalies; and wherein said second instruments are energized only in response to signals generated by said signal processing circuitry.

2. An instrument pig according to claim 1 wherein said first and second instruments are arranged in a plurality of closely spaced heads located circumferentially about said pig body and in a plane perpendicular the axis of the pipeline.

3. An instrument pig according to claim 1 wherein said first instruments are Hall-effect devices.

4. An instrument pig according to claim 1 wherein said magnets are affixed at opposed ends of elongated armatures that are in spaced apart parallel planes each including the pipeline axis, the armatures being radially positionably supported to said pig body, said first and second instruments being supported by the armatures.

5. An instrument pig according to claim 4 wherein said armatures and magnets are arranged such that mutual magnetic repulsion attains outward radial displacement towards the pipeline inner cylindrical wall.

6. An instrument pig according to claim 4 including spacers affixed to said armatures for engaging the pipeline interior wall and thereby supporting said magnets and said first and second instruments in close, predetermined spacing with respect to the pipeline interior wall.

7. An instrument pig according to claim 4 wherein said armatures are each supported to said body by link arms.

8. An instrument pig according to claim 1 wherein said first instruments are responsive to detected reluctance variations as the pig is moved through the pipeline.

9. A pipeline pig according to claim 1 wherein said second instruments are responsive to detected induced current variations in the pipeline interior surface.

10. A method of determining the characteristics of the interior and exterior surfaces of a metal pipeline comprising the steps of:
(a) moving an axially supported pig body through a pipeline;
(b) by means of magnets carried by the pig body magnetically saturating a circumferentially zone of the pipeline that moves with the pig;
(c) continuously measuring changes of reluctance in the moving circumferential zone to provide indications of the presence and size of anomalies in the pipeline interior or exterior surfaces;
(d) electrically energizing a plurality of pulse coils to induce eddy currents in the internal surface of said moving circumferential zone of the pipeline;
(e) by means of a plurality of sensing coils each paired with a said pulsed coil measuring said eddy currents to determine the presence or absence of anomalies in the pipeline interior surface;
(f) comparing the results of steps (c) and (e) in signal processing circuitry to determine whether the anomaly detected in step (c) is on the exterior or interior surface of the pipeline;
(g) recording the results of steps (c) and (f) to provide information as to the occurrence, size and exterior/interior locations of pipeline wall anomalies; and
(h) energizing said plurality of pulse coils in step (d) only in response to signals generated by said signal processing circuitry.

11. A method according to claim 10 in which step (c) and (e) are carried out by instruments arranged in a plurality of closely spaced heads located circumferentially about said pig body and in a plane perpendicular the axis of the pipeline.

12. A method according to claim 10 in which step (c) is carried out using Hall-effect devices.

13. A method according to claim 10 wherein step (b) is carried out by magnets affixed at opposed ends of elongated armatures that are spaced apart in parallel planes of the pipeline axis and radially displaceably supported to the pig body.

14. A method according to claim 13 including arranging said armatures so that the mutual magnetic repulsion of the magnets supported thereon results in radially biasing said armatures and instruments affixed thereon towards the pipeline inner, cylindrical surface.

15. A method according to claim 14 including affixing spacers to said armatures for engaging said pipeline inner cylindrical surface for thereby supporting said magnets and said instruments in close, predetermined spacing with respect to said pipeline inner cylindrical surface.

16. A method according to claim 13 including affixing said armature to said pig body by pivotal link arms.

* * * * *